(12) United States Patent
Amamiya et al.

(10) Patent No.: US 11,249,041 B2
(45) Date of Patent: Feb. 15, 2022

(54) OIL DETERIORATION DETECTOR, SENSOR COVER OF OIL DETERIORATION DETECTOR, AND METHOD OF MEASURING DEGREE OF OIL DETERIORATION

(71) Applicant: ATAGO CO., LTD., Tokyo (JP)

(72) Inventors: Hideyuki Amamiya, Tokyo (JP); Akihito Kubota, Saitama (JP)

(73) Assignee: ATAGO CO., LTD., Tokyo (JP)

( * ) Notice: Subject to any disclaimer, the term of this patent is extended or adjusted under 35 U.S.C. 154(b) by 0 days.

(21) Appl. No.: 17/048,851

(22) PCT Filed: Apr. 19, 2019

(86) PCT No.: PCT/JP2019/016896
§ 371 (c)(1),
(2) Date: Oct. 19, 2020

(87) PCT Pub. No.: WO2019/203360
PCT Pub. Date: Oct. 24, 2019

(65) Prior Publication Data
US 2021/0148847 A1    May 20, 2021

(30) Foreign Application Priority Data

Apr. 20, 2018  (JP) .............................. JP2018-081574
Aug. 21, 2018  (JP) .............................. JP2018-154497

(51) Int. Cl.
*G01N 27/22*  (2006.01)
*G01N 33/03*  (2006.01)

(52) U.S. Cl.
CPC ........... *G01N 27/226* (2013.01); *G01N 33/03* (2013.01)

(58) Field of Classification Search
CPC combination set(s) only.
See application file for complete search history.

(56) References Cited

U.S. PATENT DOCUMENTS 6,091,484 A     7/2000  Vénica et al.
6,374,797 B1 *  4/2002  Fischer .................. F01M 11/03
                                              123/196 R (Continued)

FOREIGN PATENT DOCUMENTS

JP      6-201649 A       7/1994
JP   2000-338074 A      12/2000

(Continued)

OTHER PUBLICATIONS

International Search Report for PCT/JP2019/016896 dated Jul. 16, 2019 (PCT/ISA/210).

(Continued)

*Primary Examiner* — Alvaro E Fortich
(74) *Attorney, Agent, or Firm* — Sughrue Mion, PLLC

(57) ABSTRACT

Disclosed is a device including a sensor configured to measuring an electrical characteristics of oil; a main body having the sensor in a sideward-facing orientation at one end of an elongated shape thereof; and a sensor cover having a base part configured to be attached to the main body; a tip head part having an arcuate shape or an annular shape being greater in size in a radial direction with respect to the sensor, disposed in a manner protruding at a tip side of the main body with respect to the sensor; and a connection part including a first connecting pillar connecting the base part and the tip head part and a second connecting pillar having a width smaller than a width the first connecting pillar.

19 Claims, 12 Drawing Sheets

(56) References Cited

U.S. PATENT DOCUMENTS

| | | | |
|---|---|---|---|
| 6,469,521 B1 | 10/2002 | Klün et al. | |
| 8,829,928 B2 | 9/2014 | Gonzalez et al. | |
| 2002/0113596 A1* | 8/2002 | Horie | G01N 33/2888 |
| | | | 324/438 |
| 2003/0060984 A1* | 3/2003 | Takezawa | G01N 21/3577 |
| | | | 702/28 |
| 2003/0155935 A1 | 8/2003 | Klun | |
| 2012/0062251 A1 | 3/2012 | Gonazalez et al. | |
| 2015/0027205 A1 | 1/2015 | Brugger | |
| 2016/0320325 A1 | 11/2016 | Derr | |
| 2017/0276629 A1 | 9/2017 | Amamiya et al. | |
| 2018/0120248 A1* | 5/2018 | Akuzawa | G01N 27/121 |

FOREIGN PATENT DOCUMENTS

| | | |
|---|---|---|
| JP | 2003-250708 A | 9/2003 |
| JP | 2013-541710 A | 11/2013 |
| JP | 2017-032352 A | 2/2017 |
| WO | 2016/185524 A1 | 11/2016 |

OTHER PUBLICATIONS

Communication dated Nov. 24, 2021, from the European Office in European Application No. 19788228.5.
Atago Catalog: "Frying Oil Monitor", Mar. 31, 2016, XP55861698, retrieved from https://cwtc.com.pf/cwtc-old/downloads/Catalogs-FINAL-March-2016/Atago/Frying-Oil-Monitor-DOM-24.pdf, (3 pages total).

* cited by examiner

FIG. 2
(a)
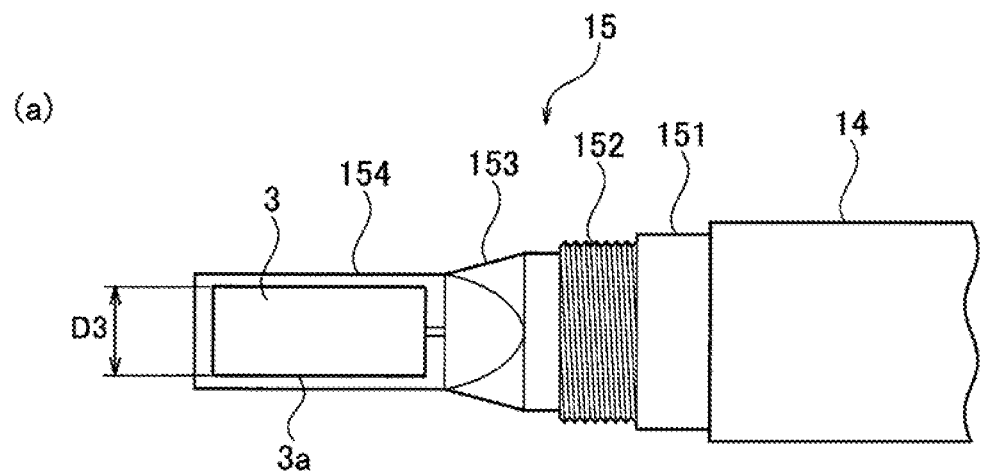
(b)
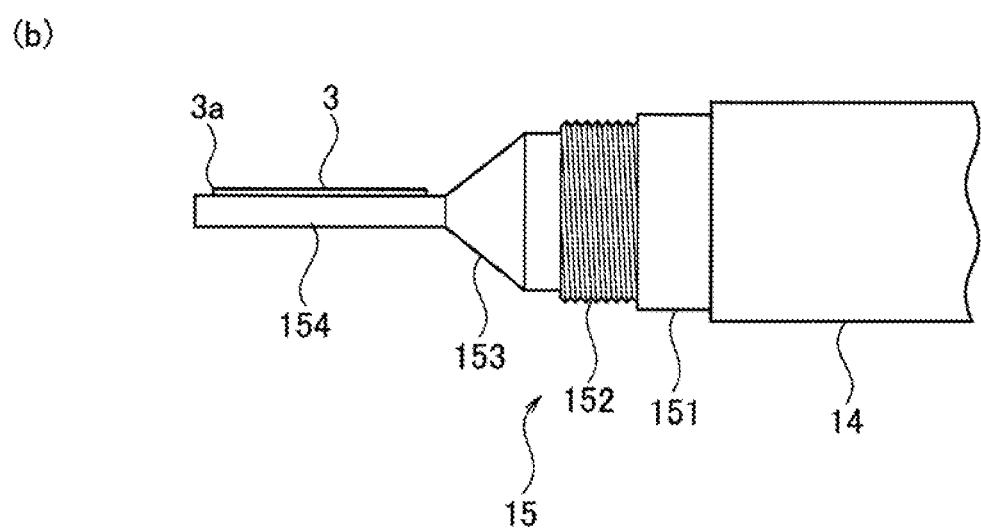

FIG. 8
(a)
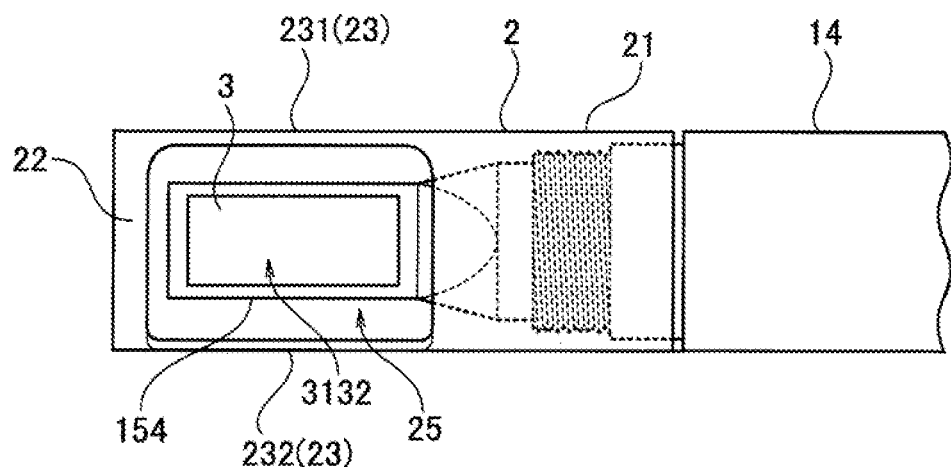
(b)
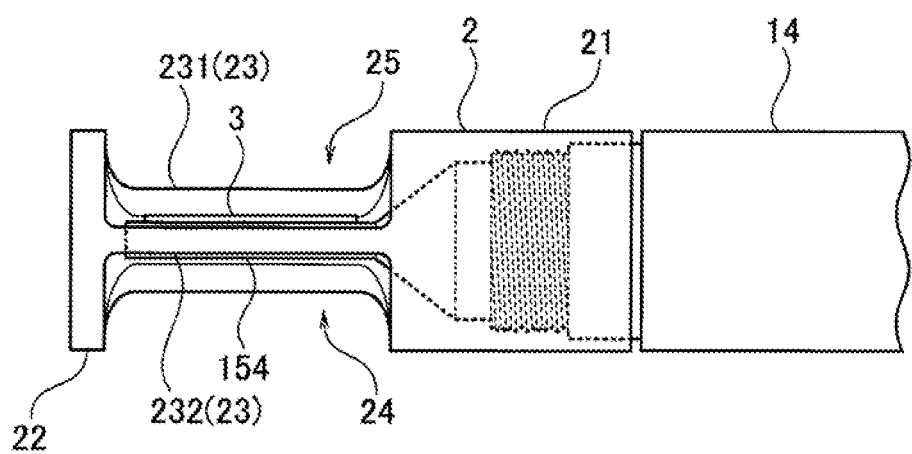

FIG. 13
(a)
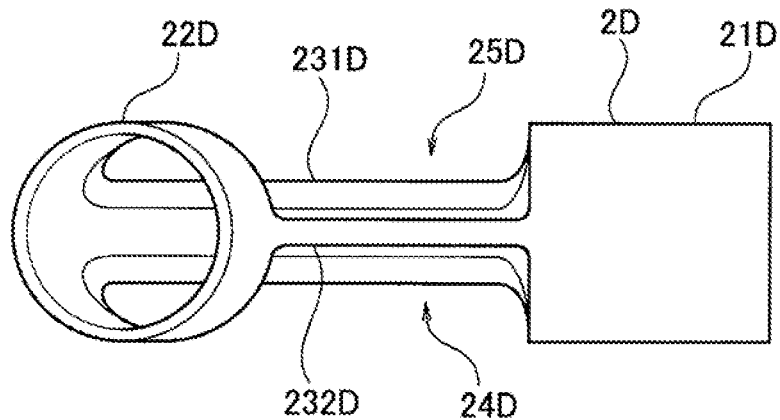
(b)
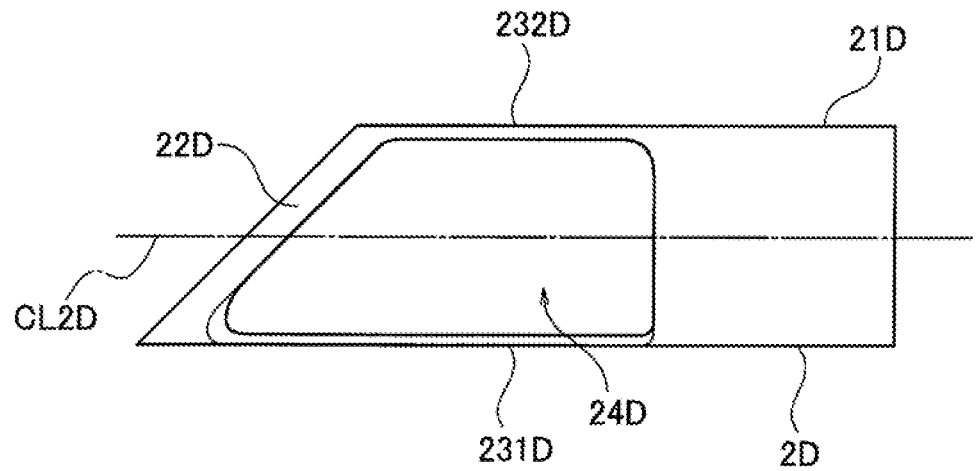

OIL DETERIORATION DETECTOR, SENSOR COVER OF OIL DETERIORATION DETECTOR, AND METHOD OF MEASURING DEGREE OF OIL DETERIORATION

CROSS REFERENCE TO RELATED APPLICATIONS

This application is a National Stage of International Application No. PCT/JP2019/016896 filed Apr. 19, 2019, claiming priority based on Japanese Patent Application No. 2018-081574 filed Apr. 20, 2018 and Japanese Patent Application No. 2018-154497 filed Aug. 21, 2018.

TECHNICAL FIELD

The present invention relates to an oil deterioration detector, a sensor cover of the oil deterioration detector, and a method of measuring degree of oil deterioration.

RELATED ART

An oil deterioration detector for detecting a degree of deterioration of oil based on the electrical characteristics of oil is known.

The oil deterioration detecting device described in Patent Literature 1 is provided with a sensor having electrodes for measuring an electrostatic capacity in the oil, and is configured to calculate a degree of deterioration of the oil based on the electrostatic capacity in the oil to be evaluated.

Further, a fryer described in Patent Literature 2 includes a sensor having an electrode at a position where the fryer is immersed in the cooking oil of the oil pan, and has a deterioration detection function for obtaining a degree of deterioration of the cooking oil from electric information measured by the sensor in a state where the fryer is immersed in the cooking oil in the oil pan.

When the oil is an edible oil, it is generally performed to measure the electrostatic capacity in the oil to be evaluated by using an electrostatic capacity sensor, to obtain a TPM (Total Polar Materials) value (%) indicating a polar molecular weight contained in the oil from the measurement result, and to evaluate a degree of deterioration.

Further, Patent Literature 3 describes a technique of measuring a voltage between a pair of electrodes in an oil and obtain a degree of deterioration of the oil based on the measured voltage.

CITATION LIST

Patent Literature

Patent Literature 1: JP 2017-032352 A
Patent Literature 2: JP 2003-250708 A
Patent Literature 3: JP H06-201649 A

SUMMARY OF INVENTION

Technical Problem

A handheld oil deterioration detector, which can evaluate a degree of deterioration of oil stored in a fryer without a sensor or a degree of deterioration of cooking oil used when cooking fried food in a pot of a general household by a TPM value based on the electric characteristics, for example, electrostatic capacity, is sold.

The handheld oil deterioration detector has a main body which can be gripped, a sensor support part provided on the tip side of the main body, a sensor attached to the sensor support part, and a control part which obtains a TPM value based on a value measured by the sensor.

A user holds the main body, dips the sensor support part to which the sensor is immersed into oil to be measured, and measures the electrostatic capacity in the dipped state. The control part determines the degree of deterioration of the oil to which the oil deterioration detector is immersed, based on the measured electrostatic capacity and outputs it to the outside.

In this oil deterioration detector, since the sensor is attached to a sensor support part at the tip of the main body, depending on the handling situation of the user, there is a considerable possibility that the sensor breaks by hitting the sensor support part against a bottom of the pot or a wall surface of the oil pan of the fryer. Therefore, it is considered to attach a protective cover for protecting the sensor.

On the other hand, if other kinds of oil measured previously remain on a surface of an electrode of the sensor, it becomes difficult to obtain an accurate measurement value by this measurement.

Therefore, although it is desired to clean the electrode surface every time after the measurement is performed, the protective cover may hinder the cleaning operation.

For this reason, there has been a demand for an oil deterioration detector to achieve both of the following: the sensor is protected and hard to break; and the cleaning operation is easy.

An object of the present invention is to provide an oil deterioration detector, a sensor cover of the oil deterioration detector, and a method of measuring a degree of oil deterioration, in which the sensor is hard to break and a cleaning work is facilitated.

Solution to Problem

The oil deterioration detector according to a first aspect of the present invention includes: a sensor configured to measure the electrical characteristics of an oil; a main body having an elongated shape and having the sensor in a sideward-facing orientation at one end of the elongated shape thereof; and a sensor cover configured to be attached to the main body. The sensor cover has a tip with an arcuate shape or an annular shape being greater in size in a radial direction with respect to the sensor. At a position on the sensor cover corresponding to the sensor on the main body in a longitudinal direction, an opening having a width equal to or greater than a width of the sensor in a side view is opened.

The oil deterioration detector according to a second aspect of the present invention includes: a sensor configured to measure electrical characteristics of an oil; a main body having an elongated shape and having the sensor in a sideward-facing orientation at one end of elongated shape thereof; and a sensor cover including a base part configured to be attached to the main body, a tip head part having an arcuate shape or an annular shape being greater in size in a radial direction with respect to the sensor and disposed in a manner protruding at a tip side of the main body with respect to the sensor, and a connection part including a first connecting pillar connecting the base part and the tip head part and a second connecting pillar having a width smaller than a width of the first connecting pillar. The sensor cover is at a first circumferential position where the connection part covers at least a part of the sensor.

The oil deterioration detector according to a third aspect of the present invention includes: a sensor configured to measure electrical characteristics of an oil; a main body having an elongated shape and having the sensor in a sideward-facing orientation at one end of the elongated shape thereof; and a sensor cover including a base part configured to be attached to the main body, a tip head part having an arcuate shape or an annular shape being greater in size in a radial direction with respect to the sensor, disposed in a manner protruding at a tip side of the main body with respect to the sensor and a connection part connecting the base part and the tip head part at only one place. The sensor cover is at a first circumferential position where the connection part covers at least a part of the sensor.

The sensor cover according to the second and third aspects may be rotatable relative to the main body between the first circumferential position and a second circumferential position where the connection part does not completely cover the sensor. Further, the sensor cover may be rotatable and detachable with respect to the main body by screwing screws.

A sensor cover according to a fourth aspect of the present invention is a sensor cover configured to be attached to an oil deterioration detector, the oil deterioration detector comprising a sensor configured to measure electrical characteristics of an oil; and a main body having an elongated shape and having the sensor in a sideward-facing orientation at one end of the elongated shape thereof, and configured to detect a degree of deterioration of oil from the electrical characteristics. In the state of being attached to the oil deterioration detector, a tip of the sensor cover protrudes at a tip side of the main body, and the tip of the sensor cover has an arcuate shape or an annular shape being equal to or greater in size in a radial direction with respect to the sensor. The sensor cover includes an opening opened at a position corresponding to the sensor on the main body in a longitudinal direction and having a width wider than a width of the sensor in a side view.

A method of measuring degree of oil deterioration according to a fifth aspect of the present invention is a method for measuring the deterioration degree of an oil heated or kept warm by an IH heating device by an oil deterioration detector. The method of measuring degree of oil deterioration uses an oil deterioration detector comprising a sensor configured to measure electrical characteristics of an oil and a main body having an elongated shape and having the sensor in a sideward-facing orientation at one end of the elongated shape thereof; brings the sensor cover into an attached state with the main body of the oil deterioration detector so as the sensor is arranged inside the sensor cover, where the sensor cover is made of a material that generates an eddy current so as to cancel an alternating magnetic flux while the sensor cover is placed in a space where the alternating magnetic flux is generated; and measures the electric characteristics with the sensor while the sensor is immersed in the oil at the attached state of the sensor cover.

The sensor cover may have a base part configured to be attached to the main body; a tip head part having an arcuate shape or an annular shape being greater in size in a radial direction with respect to the sensor, disposed in a manner protruding at a tip side of the main body with respect to the sensor in a state of being attached to the main body; and a connection part including a first connecting pillar connecting the base part and the tip head part and a second connecting pillar having a width smaller than the first connecting pillar. Further, the sensor may be oriented toward the side of the main body, and the sensor cover may be in a state in which the connection part is at a first circumferential position covering at least a part of the sensor with respect to the main body. The sensor cover may be rotatable relative to the main body between the first circumferential position and a second circumferential position where the connection part does not completely cover the sensor; and cleaning of the sensor may be performed while the sensor cover positioned at the second circumferential position.

The oil deterioration detector according to a sixth aspect of the present invention includes: a sensor configured to measure an electrical characteristics of an oil; a main body having an elongated shape and having the sensor in a sideward-facing orientation at one end of the elongated shape thereof; a sensor cover configured to be attached to the main body and is made of a material that generates an eddy current so as to cancel an alternating magnetic flux while the sensor cover is placed in a space where the alternating magnetic flux is generated. The sensor is arranged inside the sensor cover.

The main body may have the sensor in a sideward-facing orientation with respect to the main body; and the sensor cover may include a tip protruding at a tip side of the main body and the tip of the sensor cover may have an arcuate shape or an annular shape being equal to or greater in size in a radial direction with respect to the sensor, and the sensor cover may include an opening opened at a position corresponding to the sensor on the main body in a longitudinal direction and may have a width wider than a width of the sensor in a side view.

The main body may have the sensor in a sideward-facing orientation with respect to the main body. The sensor cover may include a base part configured to be attached to the main body, a tip head part having an arcuate shape or an annular shape being greater in size in a radial direction with respect to the sensor, disposed in a manner protruding at a tip side of the main body with respect to the sensor, and a connection part including a first connecting pillar connecting the base part and the tip head part and a second connecting pillar having a width smaller than the first connecting pillar. Further, the sensor cover may be at a first circumferential position with respect to the main body where the connection part covers at least a part of the sensor.

The main body may have the sensor in a sideward-facing orientation with respect to the main body. The sensor cover may include a base part configured to be attached to the main body, a tip head part having an arcuate shape or an annular shape being greater in size in a radial direction with respect to the sensor, disposed in a manner protruding at a tip side of the main body with respect to the sensor, and a connection part connecting the base part and the tip head part at only one place. Further, the sensor cover may be at a first circumferential position with respect to the main body where the connection part covers at least a part of the sensor.

The sensor cover may be rotatable relative to the main body between the first circumferential position and a second circumferential position where the connection part does not completely cover the sensor.

The sensor cover may be rotatable and detachable with respect to the main body by screwing screws.

Advantageous Effects of Invention

According to the present invention, the sensor is less likely to be broken and cleaning work is facilitated.

BRIEF DESCRIPTION OF DRAWINGS

FIG. 2(a) is a front view and FIG. 2(b) is a side view of the oil deterioration detector 51 including a sensor support section 15 and its vicinity.

FIGS. 4(a), 4(b), and 4(c) are figures illustrating a third-angle projection of a sensor cover 2 detachably attached to a tip of a main body 1 of the oil deterioration detector 51, wherein FIG. 4(a) is a front half cross-sectional view, FIG. 4(b) is a side view, and FIG. 4(c) is a cross-sectional view at the IVc-IVc position illustrated in FIG. 4(a).

FIG. 6(a) and FIG. 6(b) are views corresponding to FIG. 2(a) and FIG. 2(b) illustrating a state in which the sensor cover 2 is attached to the main body 1 of the oil deterioration detector 51, wherein FIG. 6(a) is a front view and FIG. 6(b) is a side view.

FIGS. 8(a) and 8(b) are views illustrating a state in which a mounting position around the axis of the sensor cover illustrated in FIG. 6(a) and FIG. 6(b) is rotated by 90°; FIG. 8(a) is a front view, and FIG. 8(b) is a side view.

FIGS. 9(a), 9(b), and 9(c) are views illustrating a sensor cover 2A, which is a first variation of the sensor cover 2, wherein FIG. 9(a) is a front half cross-sectional view, FIG. 9(b) is a side view, and FIG. 9(c) is a cross-sectional view at the IXc-IXc position illustrated in FIG. 9(a).

FIG. 12(a) and FIG. 12(b) is a cross-sectional view of a sensor cover 2C, a third variation of the sensor cover 2, in which FIG. 12(a) is a cross-sectional view at the rotational position in a circumferential direction at a first position and FIG. 12(b) is a cross-sectional view at the rotational position in the circumferential direction at a second position.

FIG. 13(a) and FIG. 13(b) are plan views illustrating a sensor cover 2D, which is a fourth variation of the sensor cover 2, and FIG. 13(a) is a front view and FIG. 13(b) is a side view.

DESCRIPTION OF EMBODIMENTS

An embodiment of an oil deterioration detector will be described with reference to an oil deterioration detector 51 of an embodiment.

The oil deterioration detector 51 is a handheld device. The user grips it, and is used by immersing a tip having an electrostatic capacity sensor in the oil stored in a container such as a fryer or a pot.

The oil deterioration detector 51 is a device for obtaining and displaying a TPM value by a well-known method on the basis of the electrostatic capacity measured while the tip is immersed in the oil. That is, the oil deterioration detector 51 is a device for detecting the degree of deterioration of the oil.

Figure 1:
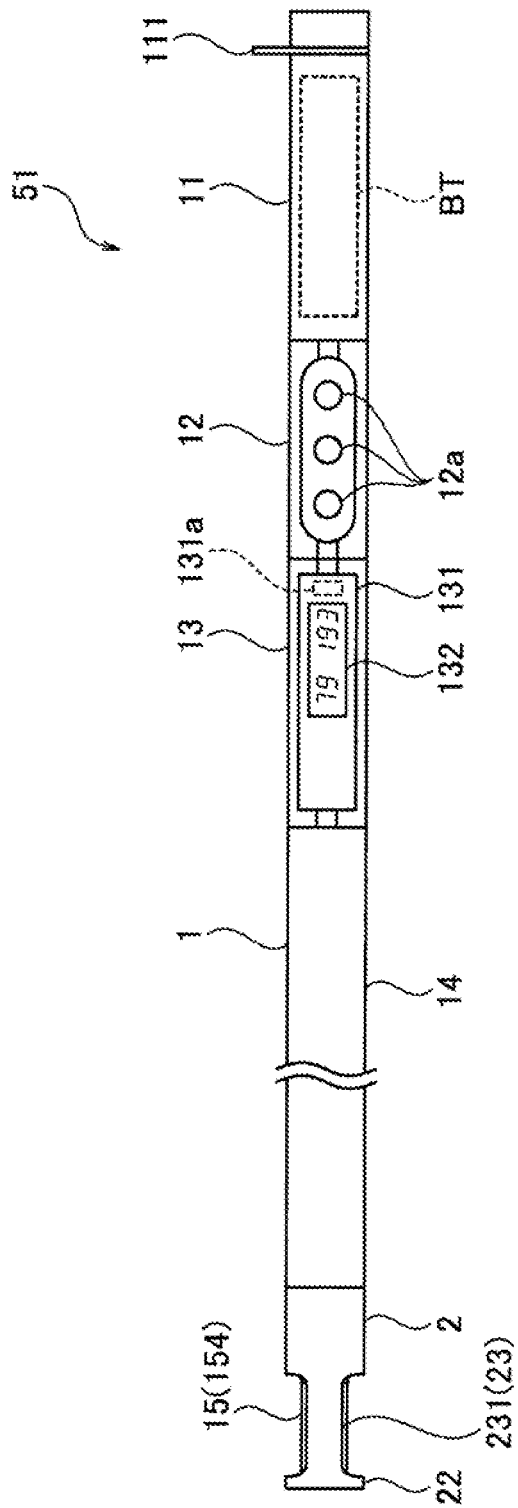
FIG. 1 is an external front view of an oil deterioration detector 51, which is an embodiment of the oil deterioration detector according to the present invention.

As illustrated in FIG. 1, the oil deterioration detector 51 has a main body 1 with a straight rod-shape and a sensor cover 2 detachably attached to a tip part of the main body 1.

The main body 1 has a grip section 11, an operation section 12, a core section 13, a relay section 14, and a sensor support section 15 in this order from the rear end side.

A casing of the operation section 12 and the core section 13 is made of transparent resin. An example of the transparent resin is polycarbonate.

A casing of the grip section 11 and the relay section 14 is made of metal. An example of the metal is a stainless steel alloy.

The grip section 11 is a section to be gripped by a user's hand. Inside the grip section 11, a battery BT such as a dry cell serving as a power source of the oil deterioration detector 51 is accommodated.

The grip section 11 is also provided with a strap holder 111 projecting outward of a diameter and capable of fastening a strap.

The operation section 12 has a plurality of operation buttons 12a for a user to give instructions such as turning on/off a power supply, switching an operation mode, and switching a display mode.

The core section 13 has a circuit board 131 accommodated therein. On the circuit board 131, a controller 131a including a central processing unit (CPU) and a display 132 are mounted. The display 132 includes a display element such as a liquid crystal element or an organic EL element, and displays a number, a mark, etc.

The controller 131a controls an operation of the oil deterioration detector 51 in accordance with an operation of the operation section 12, and displays an operation state (Battery level, etc.) on the display 132.

The controller 131a obtains a TPM value based on a detection signal from a sensor 3 to be described later, and displays the value on the display 132.

Since the casing of the core section 13 is transparent, the user can view the display 132 accommodated inside the core section 13 from the outside.

The sensor support section 15 is disposed on a tip side of the core section 13 with the relay section 14 interposed between the core section 13 and the sensor support section 15.

FIG. 2(a) and FIG. 2(b) illustrates the sensor support section 15 and a tip part of the relay section 14 with the sensor cover 2 removed.

The sensor support section 15 has a cover engagement part 151, a male screw part 152, an intermediate part 153, and a sensor support base 154 from the relay section 14 side.

The cover engagement part 151 is formed in a cylindrical shape having an outer diameter smaller than twice the thickness of the sensor cover 2 with respect to the outer diameter of the relay section 14.

The male screw part 152 is formed with a male screw having an outer diameter (Nominal Diameter) slightly smaller than the outer diameter of the cover engagement part 151.

The intermediate part 153 is formed to reduce its diameter and gradually change its shape from a part on the male screw part 152 side shaped in the cylindrical shape to a part having a cross section in an elongated rectangular shape.

The sensor support section 15 is connected to the elongated rectangular shaped tip end of the intermediate part 153 and extends in a plate shape, and the sensor 3 is attached to the upper surface of one surface of the sensor support section 15 as illustrated in FIG. 2(b).

The cover engagement part 151, the male screw part 152, and the intermediate part 153 have wiring holes (not illustrated) communicating in an axial direction and opening in the relay section 14 and the sensor support base 154 side.

Figure 3:
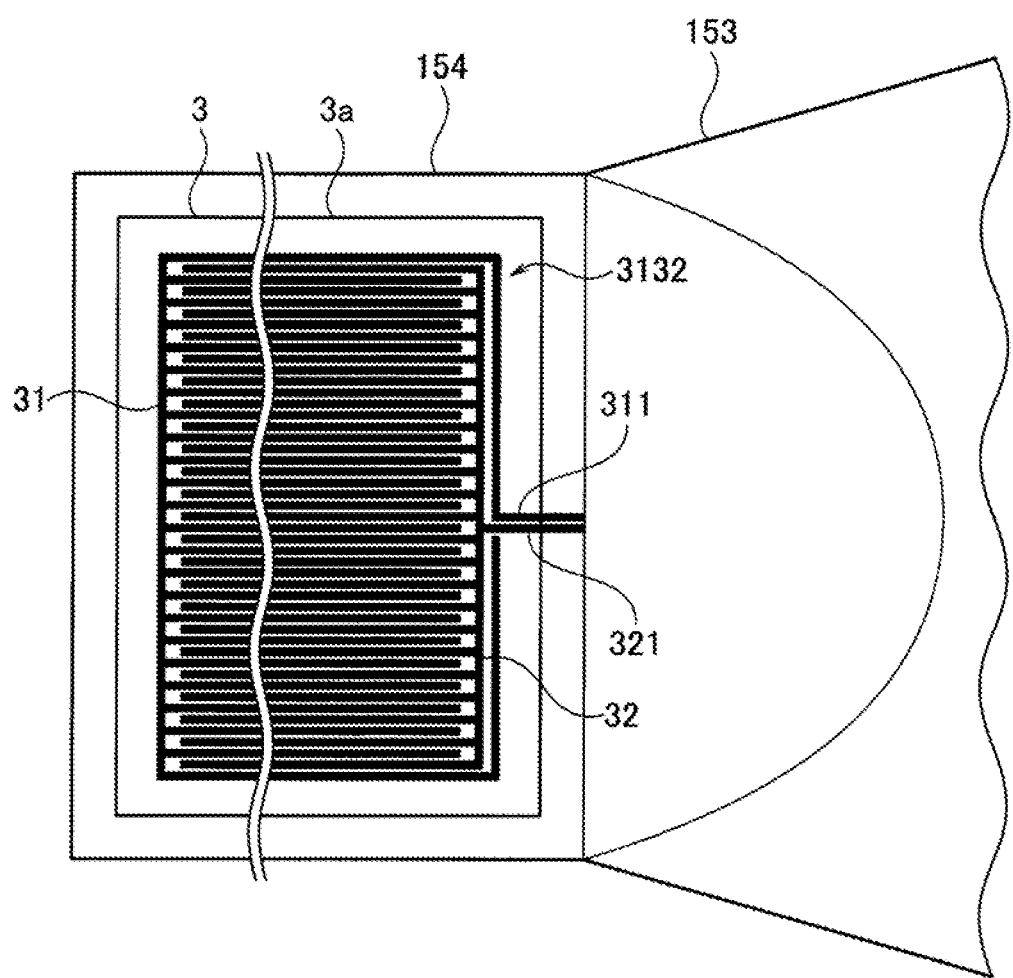
FIG. 3 is a front view of the oil deterioration detector 51 illustrating an electrode 3132 of a sensor 3.

The sensor 3 is an electrostatic capacity sensor, as illustrated in FIG. 3, and has a sensor base 3a and an electrode 3132 formed on the sensor base 3a.

The electrode 3132 is formed as a set of wiring patterns in which a pair of interdigitated electrodes, i.e., an outer interdigitated electrode 31 and an inner interdigitated electrode 32, are combined so as to enter each other in an insulated state.

The outer interdigitated electrode-wire 311, which is a wiring pattern connected to the outer interdigitated electrode 31, and the inner interdigitated electrode-wire 321, which is a wiring pattern connected to the inner interdigitated electrode 32, are connected to a lead wire (not illustrated), passing through the wiring hole and connected to the circuit board 131 through the relay section 14.

That is, the sensor 3 and the controller 131a are electrically connected to each other.

FIGS. 4(a), 4(b), 4(c), and 5 illustrate the sensor cover 2.

The sensor cover 2 is formed by cutting a metal material (e.g., SUS 316), for example, from a seamless pipe or a round bar.

The sensor cover 2 has a base part 21 with cylindrical shape arranged on a rear end side, a tip head part 22 with an annular shape arranged on a tip side, and a connection part 23 for connecting the base part 21 and the tip head part 22 in an axial direction.

The base part 21 with the cylindrical shape has an engagement part 211 fitted to the outside of the cover engagement part 151 of the main body 1 with almost no gap, and a female screw part 212 screwed to the male screw part 152.

In this embodiment, the connection part 23 is two connecting pillars, namely, a connecting pillar 231 and a connecting pillar 232.

The connecting pillar 231 and the connecting pillar 232 are formed to be spaced apart in the circumferential direction, and in this embodiment, they are formed to face each other in a radial direction of the connection part 23.

As illustrated in FIG. 4(c), a width D231, which is a width of the connecting pillar 231 in a side view, is wider (larger) than a width D232, which is a width of the connecting pillar 232 in the side view.

The width D231 is set to a value roughly corresponding to a width D3 of the sensor 3 [see FIG. 2(a)]. For example, in the side view, the width D231 is set to a value equal to or greater than the width D3. The width D232 is set to a value smaller than the width D3 (narrow width).

In the sensor cover 2, the tip head part 22 and the base part 21 are connected only by the connection part 23. That is, the sensor cover 2 has a pair of openings 24 and 25 that are spaced apart from each other across the connecting pillar 231 and the connecting pillar 232 in the circumferential direction in the axial range where the connection part 23 exists.

Further, the widths D231 and D232 of the connecting pillars 231 and 232 are set so that a greater of an opening width D24 and an opening width D25 in the side view of the opening 24 and the opening 25 [see FIG. 4(b)] is set to be a width at least equal to the width D3 of the sensor 3 or greater.

Figure 6:
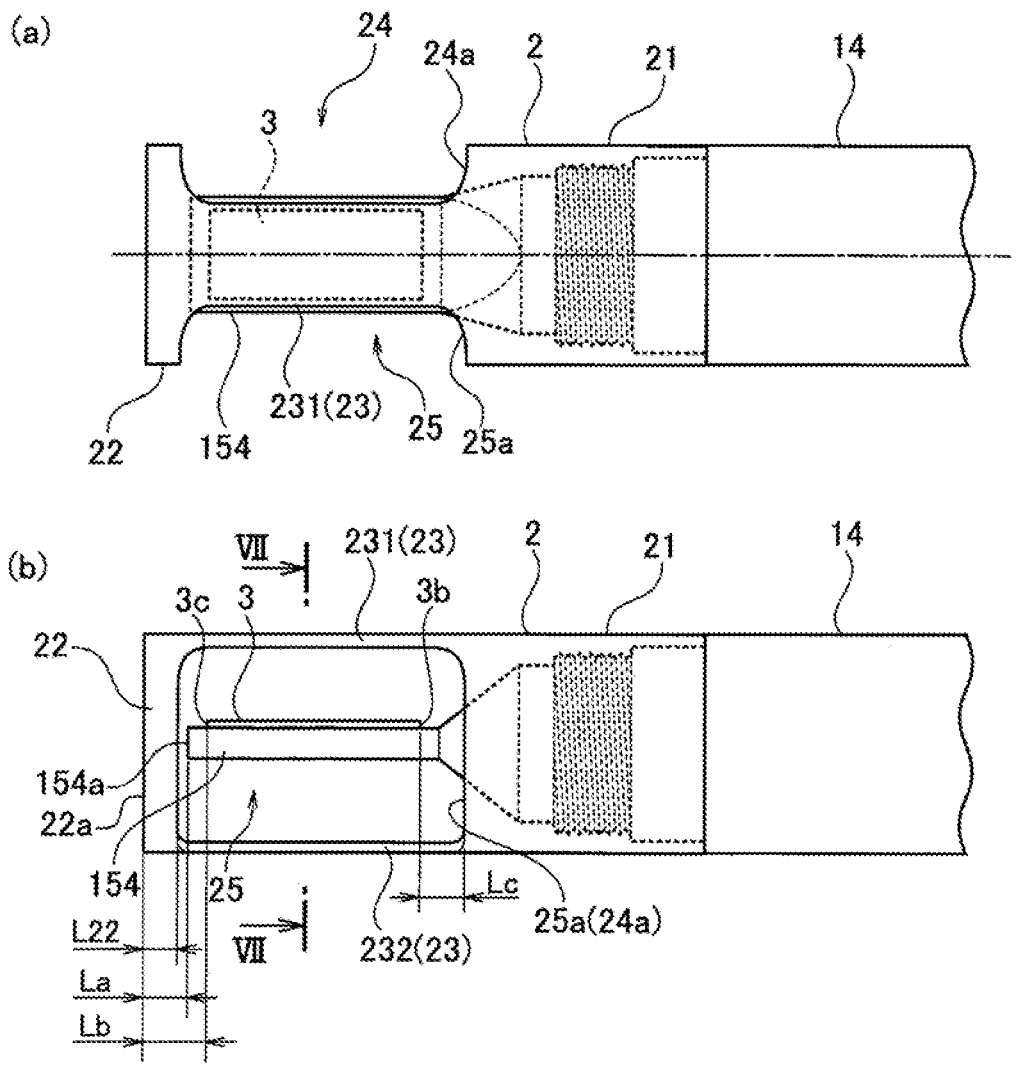

As illustrated in FIG. 6(b), a tip end 22a on the tip side of the tip head part 22 is located at a position protruding to the tip side (opposite to the relay section 14) from a tip 154a of the sensor support base 154. In this embodiment, the tip end 22a is protruded only by a distance La from the tip 154a.

As a result, when an operator inserts the oil deterioration detector 51 into an oil of a fryer or a pan, even if the tip side is erroneously hit against the flyer wall or the bottom of the pan, the tip head part 22 hits to the flyer or pan, and does not hit the sensor support base 154. Therefore, the electrode 3132 of the sensor 3 is prevented from being damaged.

A width L22, which is an axial length of the tip head part 22, is preferably equal to or less than a distance Lb, which is an axial distance between the tip end 22a and a leading end 3c of the sensor 3.

As illustrated in FIG. 6(b), it is preferable that the edges 24a and 25a of the openings 24 and 25 on the relay section 14 side are located at a same position as a trailing end 3b of the sensor 3 or at a rear end side thereof (the relay section 14 side). That is, the distance Lc illustrated in FIG. 6(b) is preferably 0 (zero) or a positive value.

Thus, when the sensor cover 2 is in a mounting reference posture and a cleaning posture to be described later, the entire longitudinal direction of the sensor 3 can be faced from the opening 24 or the opening 25.

Therefore, a cotton swab or a cloth reaches the entire longitudinal direction of the sensor 3 and a cleaning work is facilitated in the cleaning performed by the cotton swab, the cloth or the like through the openings 24 and 25.

The openings 24 and 25 are used for cleaning work, and also function as air escape when the tip side of the oil deterioration detector 51 is inserted into oil.

The sensor cover 2 is attached by screwing the female screw part 212 to the male screw part 152 while passing the sensor support base 154 inside from the tip side of the sensor support part 15.

That is, the sensor cover 2 is rotatable with respect to the main body 1.

The female screw part 212 and the male screw part 152 are managed so that the posture of the sensor cover 2 in the rotating direction always becomes a predetermined posture when the base part 21 is firmly screwed until the base part 21 abuts on the end part of the relay section 14. The predetermined posture at a first circumferential position of the sensor cover 2 is referred to as an attachment reference posture.

Figure 7:
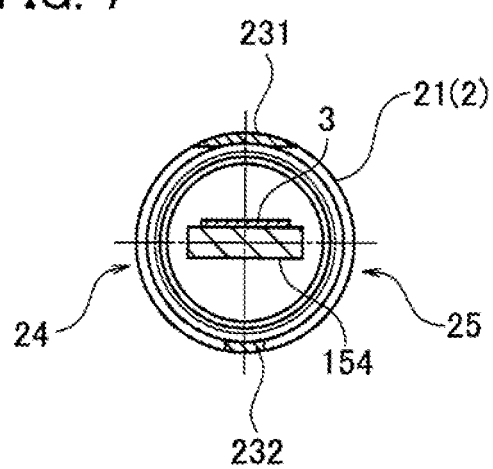
FIG. 7 is a cross-sectional view at VII-VII position illustrated in FIG. 6(b).

As illustrated in FIGS. 6(a), 6(b), and 7, the attachment reference posture of the sensor cover 2 is such that the connecting pillar 231, which is a first connecting pillar having a wider width, is positioned at an position facing and covering at least a part of the sensor 3 in a side view.

In contrast, the connecting pillar 232, which is a second connecting pillar having a narrower width, faces a surface of the sensor support base 154 on a side to which the sensor 3 is not attached.

Thus, when the sensor cover 2 is in the attachment reference posture, the sensor 3 is covered by the connecting pillar 231 in a front view [FIGS. 6(a) and 7].

Therefore, in the oil deterioration detector 51, the sensor support base 154 does not collide with a bottom of a pot or a wall surface of an oil pan in the measurement work, and the sensor 3 is prevented from being damaged.

Further, by setting the width D231 of the connecting pillar 231 and by finely adjusting the circumferential position of the attachment reference posture, as seen from the side view [FIG. 6(b)], the side surface of the sensor 3 can be faced from at least one of the opening 24 and the opening 25.

In this case, the surface of the sensor 3 can be cleaned by a cotton swab or the like through the opening 24 or the opening 25 while the sensor cover 2 remains in the attachment reference posture.

In this way, the oil deterioration detector 51 can clean the surface of the sensor 3 without removing the sensor cover 2 from the main body 1, so that the cleaning work is easy.

When cleaning the sensor 3, the sensor cover 2 may be rotated in a direction to loosen the screwing. For example, as illustrated in FIGS. 8(a) and 8(b), the screwing may be rotated about 90° in a direction in which the screw is loosened (in a counterclockwise direction as viewed from the tip side). This posture of the sensor cover 2 at a second circumferential position is referred to as a cleaning posture.

When the sensor cover 2 is in the cleaning posture, the connecting pillar 231 is at a position facing the side face of the sensor 3, and the connection part 23 opposed to the front side of the sensor 3 is not present. That is, in the front view illustrated in FIG. 8(*a*), the sensor 3 faces through the opening 25.

Thus, residual oil or the like adhering to the electrode 3132 can be removed from the front side of the sensor by using a cotton swab, cloth, or the like. Therefore, the cleaning work is easy.

As described above, the oil deterioration detector 51 does not need to remove the sensor cover 2 from the main body 1 when cleaning the sensor 3. The posture change between the attachment reference posture and the cleaning posture is only by rotating the sensor cover 2 by about 90°. Therefore, the oil deterioration detector 51 can be easily cleaned.

The sensor cover 2 has a tip head part 22 positioned on the tip side of the sensor 3, the base part 21 positioned on the rear end side of the sensor 3, and a connection part 23 connecting the tip head part 22 and the base part 21 so as to obtain conduction.

Thus, when the sensor cover 2 is placed in a space where the alternating magnetic flux is generated, an eddy current is generated in the sensor cover 2 and cancels the alternating magnetic flux.

Therefore, the inside of the sensor cover 2 becomes a shield space, which is hardly affected by the external alternating magnetic flux. That is, an internal space of the sensor cover 2 becomes a space, which is hardly affected by the external magnetic flux change.

Therefore, the oil deterioration detector 51 provided with the sensor cover 2 can measure an electrostatic capacity by the sensor 3 without being greatly affected by the alternating magnetic flux even when the oil accommodated in the oil deterioration detector 51 is heated by the so-called IH heating method in which the fryer or the pan is inductively heated by the alternating magnetic flux to raise the temperature, and can be obtain the TPM value of the oil from the measured value and output the TPM value.

Embodiments are not limited to the above-described configurations and procedures, and may be modified within the scope of the invention without departing from the spirit of the invention.

The connection part 23 may be a connection part 23A having only one connecting pillar, instead of having two connecting pillars 231 and 232 as described above.

Figure 9:
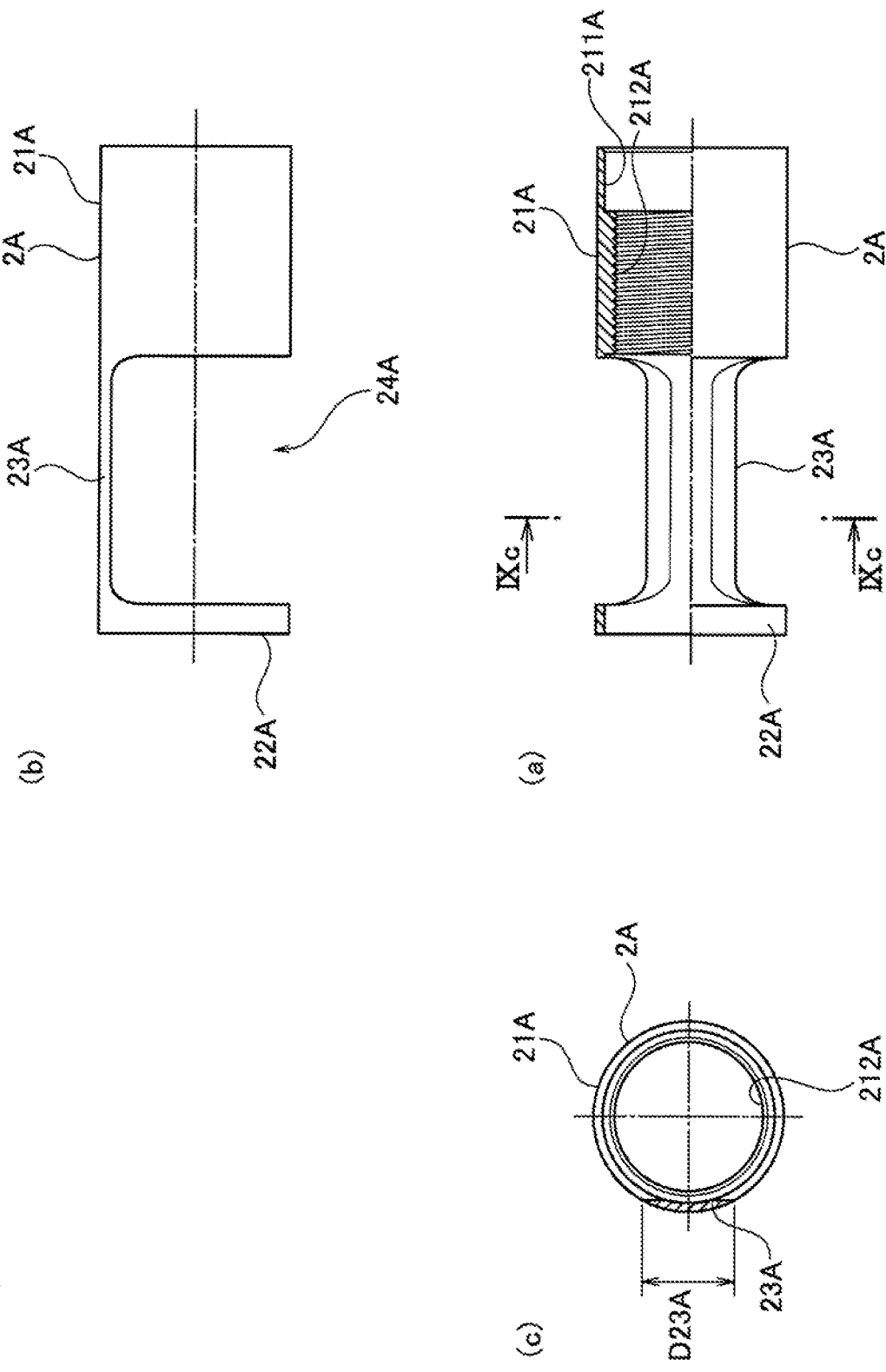

A sensor cover 2A having the connection part 23A is illustrated in FIGS. 9(*a*), 9(*b*), 9(*c*), and 10 as a first variation.

Figure 4:
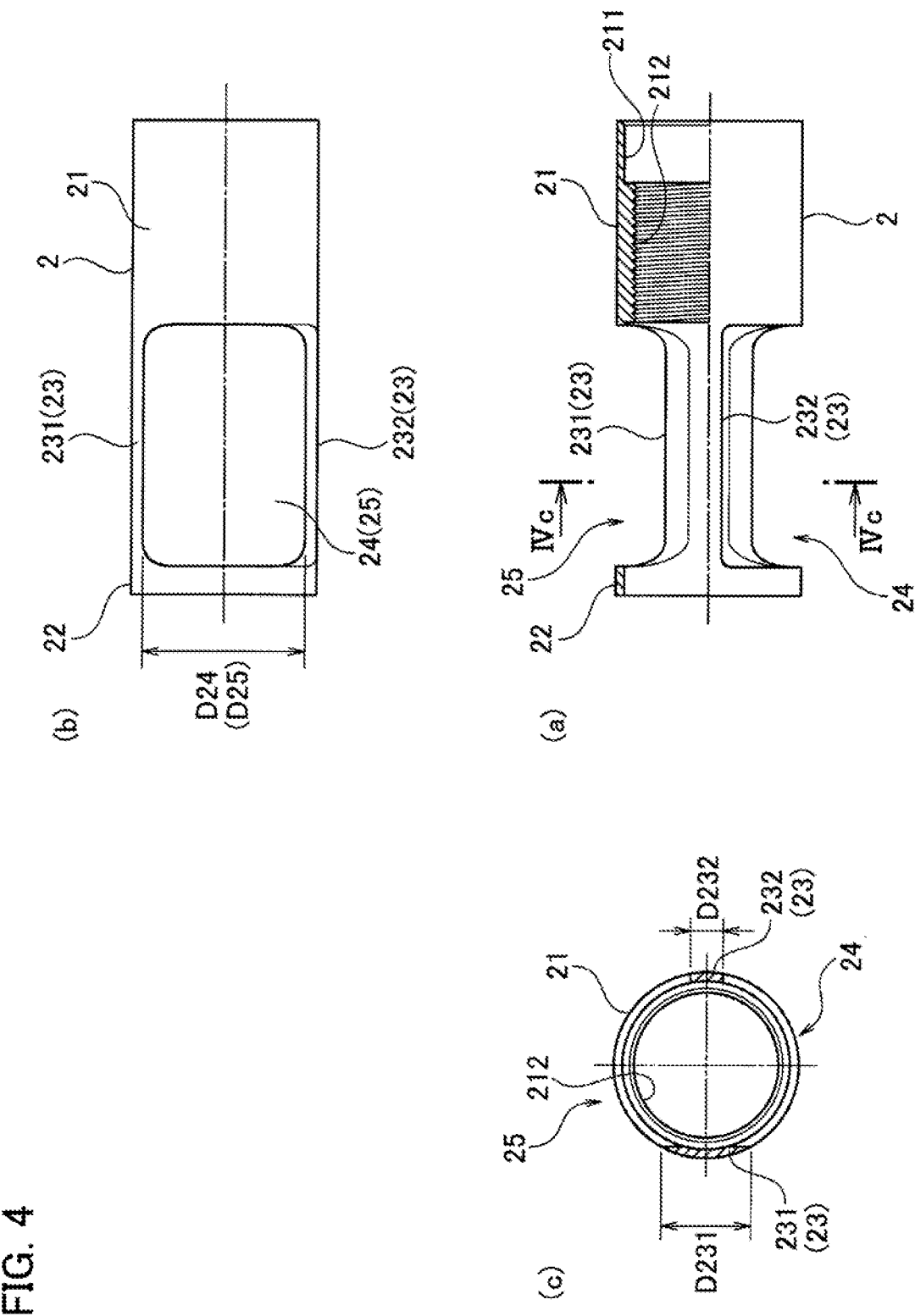
Figure 5:
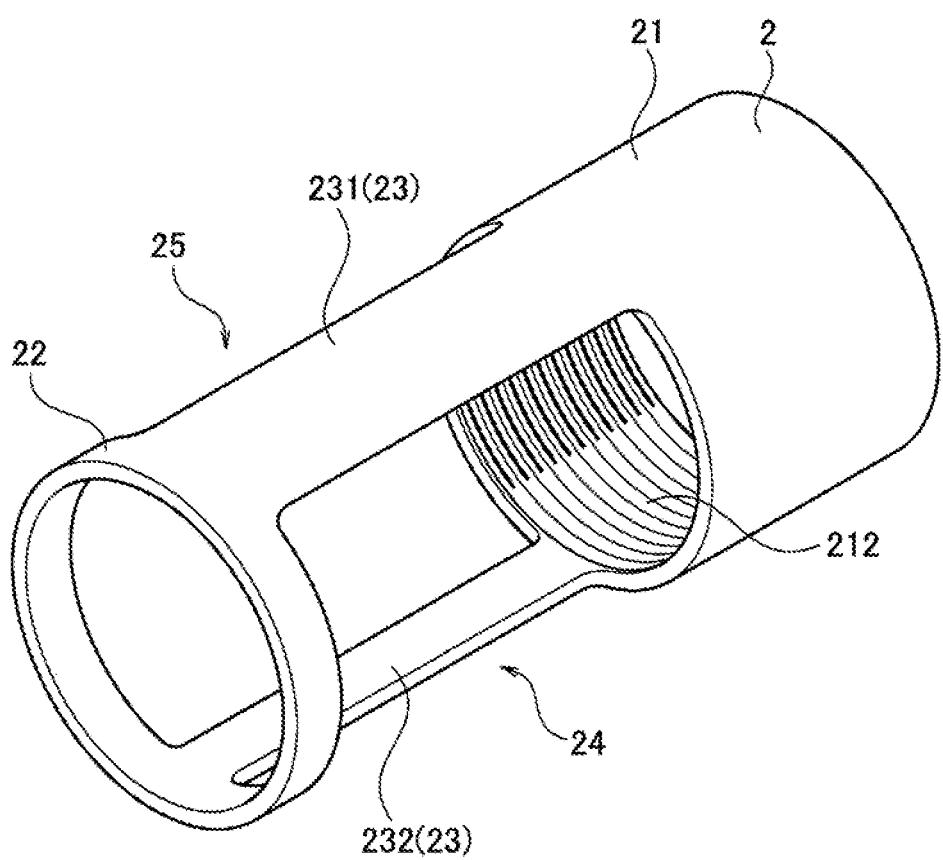
FIG. 5 is a perspective view of the sensor cover 2.
Figure 10:
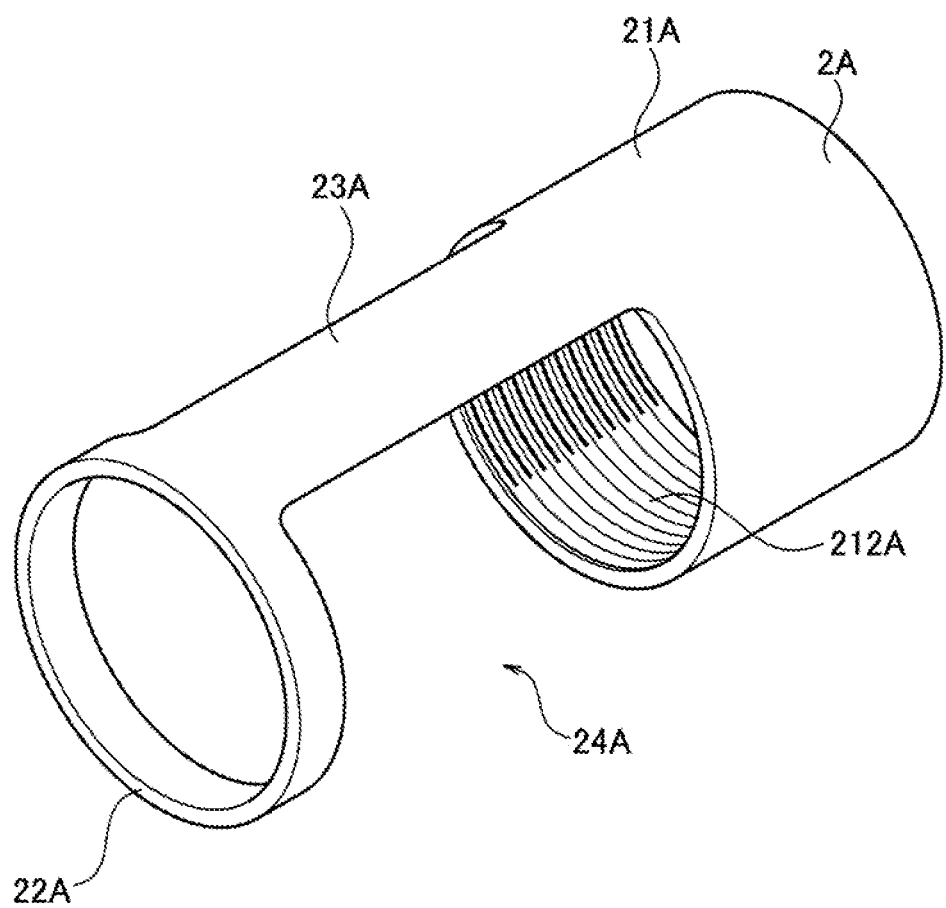
FIG. 10 is a perspective view of the sensor cover 2A.

FIGS. 9(*a*), 9(*b*), and 9(*c*) are views corresponding to FIGS. 4(*a*), 4(*b*), and 4(*c*) illustrating the sensor cover 2, and FIG. 10 is a perspective view of the sensor cover 2A.

The sensor cover 2A has a connection part 23A for connecting a tip head part 22A corresponding to the tip head part 22 and a base part 21A corresponding to the base part 21 at one place.

A width D23A in a side view of the connection part 23A is set at a value substantially corresponding to the width D3 of the sensor 3. For example, in a side view, the width D23A is set to be equal to or greater than the width D3 and equal to or less than the diameter of the sensor cover 2A. That is, a circumferential angle at which the connection part 23A can be taken is set to be less than 180° at most.

The sensor cover 2A may manage the threading positions of the male screw part 152 and the female screw part 212A so that the connection part 23A is in a posture facing the sensor 3 in the attachment reference posture attached to the main body 1.

Thus, in the attachment reference posture, the sensor 3 is covered with the connection part 23A on the front side, and is excellently protected in collision with the other members.

When the surface of the sensor 3 is cleaned from the front side, the sensor cover 2A is rotated by about 90° in the direction of loosening the screwing, for example, so that the cleaning can be easily performed in the same manner as the sensor cover 2.

The tip head part 22 of the sensor cover 2 is not limited to a completely connected and continuous annular shape, but may be formed in a substantially annular shape with a missing discontinuity. The tip head part 22 may be, for example, a so-called C-shape in the case of where discontinuous part is one place, or may be an arcuate shape in the case of two or more discontinuous parts.

Figure 11:
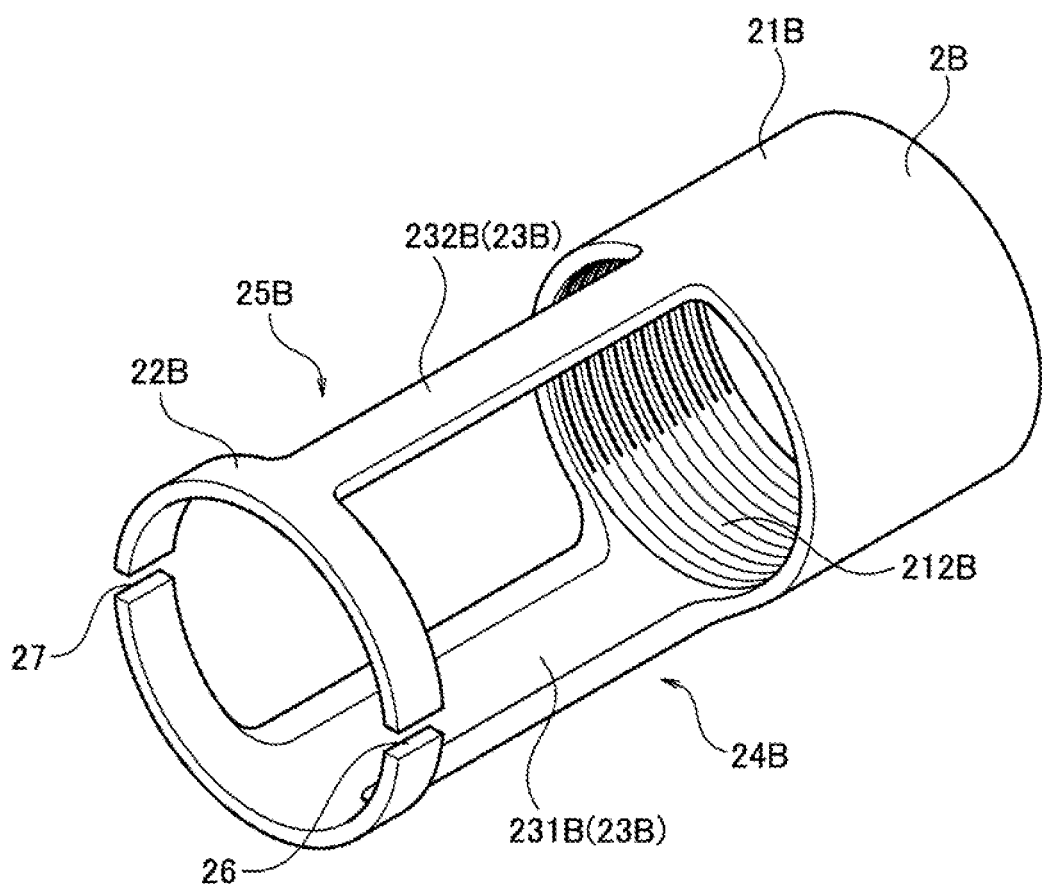
FIG. 11 is a perspective view of a sensor cover 2B, which is a second variation of the sensor cover 2.

FIG. 11 illustrates, as a second variation, a sensor cover 2B provided with a tip head part 22B having two discontinuous parts 26 and 27 facing each other in the radial direction, instead of the tip head part 22.

The sensor cover 2B has a base part 21B and a female screw part 212B respectively corresponding to the base part 21 and the female screw part 212 of the sensor cover 2. The sensor cover 2B has a connection part 23B and connecting pillars 231B and 232B, corresponding to the connection part 23 and the connecting pillars 231 and 232, respectively, thereby forming openings 24B and 25B corresponding to the openings 24 and 25.

The sensor cover 2B also has the same effect as the sensor cover 2 and the sensor cover 2A in the protection and cleaning easiness of the sensor 3.

The number of the connection part 23 is not limited to two places or one place and may be three places. That is, the sensor cover 2, may be a sensor cover 2C including a connection part 23C having connecting pillars 231C to 233C instead of having the connection part 23.

Figure 12:
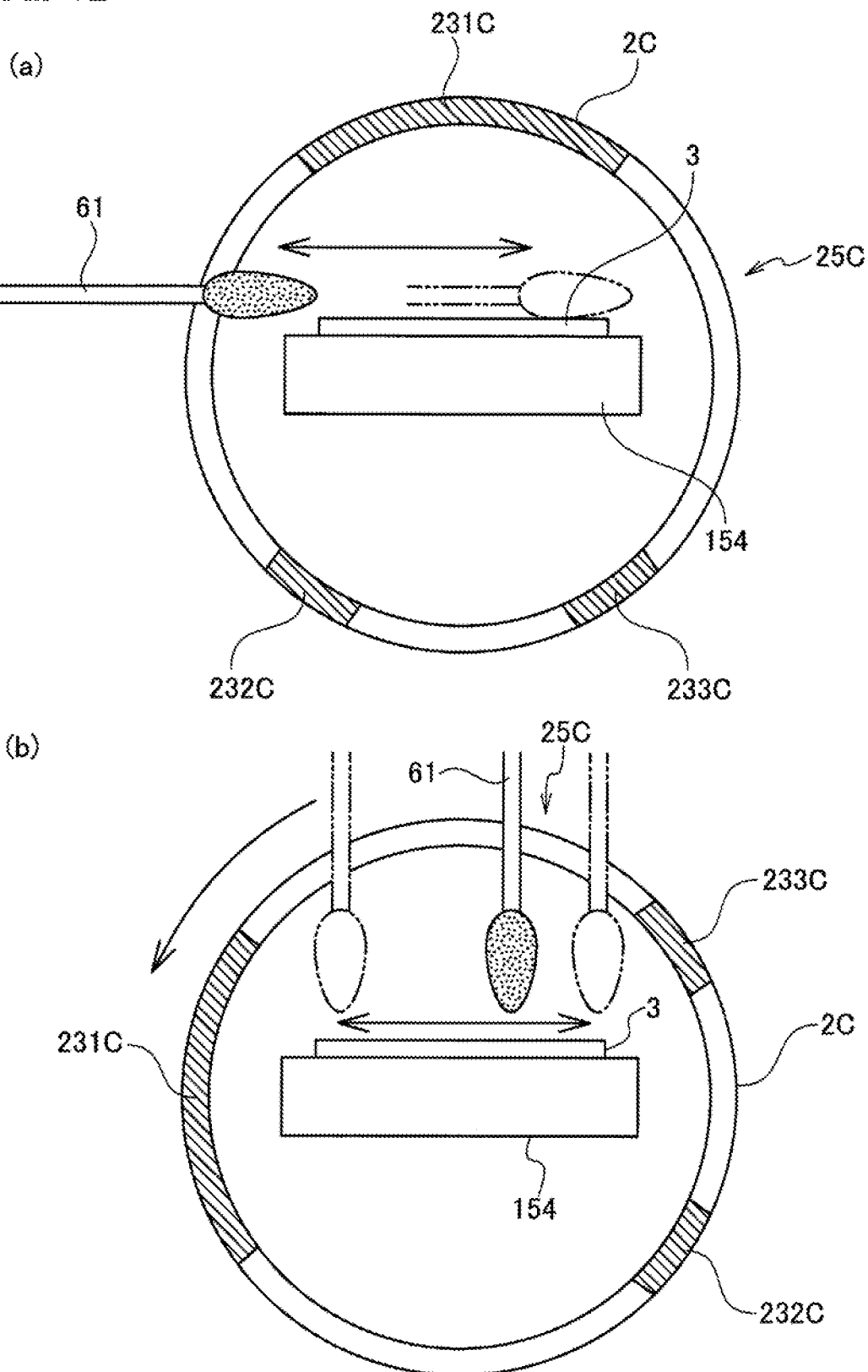

FIGS. 12(*a*) and 12(*b*) are cross-sectional view illustrating a cross-sectional shape of the sensor cover 2C at a position where the connection part 23C is formed. FIG. 12(*a*) is a cross-sectional view of an attachment reference posture, and FIG. 12(*b*) is a cross-sectional view in a cleaning posture.

The sensor cover 2C includes a connection part 23C formed with a connecting pillar 231C having a width corresponding to a width of the sensor 3, and connecting pillars 232C and 233C having a width smaller than the connecting pillar 231C.

In this embodiment illustrated in FIGS. 12(*a*) and 12(*b*), in order to obtain an opening 25C having a width corresponding to the width of the sensor 3 in the cleaning posture illustrated in FIG. 12(*b*), a circumferential interval between the connecting pillar 232C and the connecting pillar 233C is set smaller than a circumferential interval between the connecting pillar 231C and the connecting pillar 232, and a circumferential interval between the connecting pillar 231C and the connecting pillar 233C.

That is, the connecting pillars 231C to 233C are formed so as not to have the same circumferential angular pitch.

In contrast, the width of each of the connecting pillars 231C to 233C may be set to be equal to or greater than the width of the sensor 3, and the circumferential pitch to be formed may be made equal.

In this case, even if the threaded position of the female screw part 212C of the sensor cover 2C and the male screw part 152 on the main body 1 side is not managed, a cleaning tool 61 such as a cotton swab or cloth can be inserted from one side or the other side to the front surface of the sensor 3 through the opening, and the surface of the sensor 3 can be cleaned. Further, the entire front face of the sensor 3 may be not always covered by the connection part 23C, but can be covered to some extent. In addition, since the tip head part 22 is arranged at the tip side of the sensor cover 2C without change it, the sensor cover 2C can protect the sensor 3 in the same manner as the sensor covers 2A and 2B when the sensor cover 2C collides with another member.

The sensor cover 2 may be a sensor cover 2D as a fourth variation illustrated in FIGS. 13(a) and 13(b).

The sensor cover 2D has a base part 21D corresponding to the base part 21 of the sensor cover 2 and a tip head part 22D corresponding to the tip head part 22. The sensor cover 2D has connecting pillars 231D and 232D corresponding to the connecting pillars 231 and 232, respectively, thereby forming openings 24D and 25D corresponding to the openings 24 and 25, respectively.

In the sensor cover 2D, a tip head part 22D is formed along an oblique crossing direction without being orthogonal to an axial line CL2D of the sensor cover 2.

The sensor cover 2D also has the same effects as the sensor cover 2 and the sensor covers 2A to 2C in the protection and cleaning easiness of the sensor 3.

The above embodiments and variations may be combined as appropriate.

The sensor covers 2A, 2C, and 2D, which are annular in shape and has no discontinuous part and have at least a closed tip head part, are hardly affected by the change of the magnetic flux of the external space, and the electrostatic capacity of the oil contained in the container heated by IH can be measured and displayed in terms of the TPM value (%) as well as the sensor cover 2 of the embodiment.

The oil deterioration detector 51 is not limited to a device as illustrated in FIG. 1, which is formed as a whole in a straight rod shape having the same diameter.

For example, the relay section 14 may be formed to have a smaller diameter than other portions. Further, the main body 1 is not limited to a straight rod shape, and may be formed in a curved shape or a shape having a bent part.

The attachment structure of the sensor cover 2 to the main body 1 is not limited to the screwing of the screw described above. For example, a bayonet structure or an attachment structure using a setscrew may be used.

The sensor cover 2 may be integrated without being detachable from the main body 1.

In this case, it is preferable to be able to rotate between the attachment reference posture and the cleaning posture.

The sensor 3 is for measuring electrical characteristics in oil, and is not limited to measuring the electrostatic capacity described above.

The oil deterioration detector provided with the sensor cover may be configured by attaching any one of the sensor covers 2, 2A to 2D described in the embodiment and each variation in a so-called post-attachment manner to the oil deterioration detector used in a state where the sensor is exposed without the sensor cover.

The oil deterioration detector used in a state where the sensor is exposed without the sensor cover generally has the relay section 14 with an appearance formed in a rod shape that is thinner than the core section 13 and the sensor support section 15.

In such a device, either of the sensor covers 2, 2A to 2D is attached to the sensor support section 15 or the relay section 14 by a well-known technique (Fixing by screws, adhesives, welding, etc.) in a detachable or non-detachable manner.

By retrofitting the sensor cover, the damage prevention effect of the sensor and the facilitation of the cleaning work can be realized, and the electrostatic capacity can be measured even for the oil being heated or kept warm by the IH heating device, and the TPM value can be obtained.

As described above, it is to be understood that the present invention includes various embodiments not described herein. Accordingly, the technical scope of the present invention is determined only by the claimed invention as appropriate from the foregoing description.

The entire contents of Japanese Patent Application No. 2018-081574 (filed on Apr. 20, 2018) and Japanese Patent Application No. 2018-154497 (filed on Aug. 21, 2018) are incorporated herein by reference.

REFERENCE SIGNS LIST

1 Main Body
11 Grip Section; 111 Strap Holder; 12 Operation Section
12a Operation Button; 13 Core Section; 131 Circuit Board
131a Controller; 132 Display; 14 Relay Section
15 Sensor Support Section; 151 Cover Engagement Part
152 Male Screw Part; 153 Intermediate Part
154 Sensor Support Base; 154a Tip; 2, 2A, 2B, 2C, 2D Sensor Cover
21 Base Part; 211 Engagement Part; 212, 212A Female Screw Part
22, 22A, 22B, 22D Tip Head Part; 22a Tip End
23, 23A, 23C Connection Part
231, 232, 231C, 232C, 233C Connecting Pillar
24, 25, 25C Opening; 24a, 25a Edge
26, 27 Discontinuous Part
3 Sensor
3a Sensor Base; 3b Trailing End; 3c Leading End
31 Outer Interdigitated Electrode
311 Outer Interdigitated Electrode-Wire
32 Inner Interdigitated Electrode
321 Inner Interdigitated Electrode-Wire; 3132 Electrode
51 Oil Deterioration Detector; 61 Cleaning Tool; BT Battery
CL2D axis; D231, D232, D3, D23A Width
D24, D25 Opening Width; La, Lb Distance; L22 Width

The invention claimed is:

1. An oil deterioration detector comprising:
a sensor configured to measure electrical characteristics of an oil;
a main body having an elongated shape and having the sensor in a sideward-facing orientation at one end of the elongated shape thereof; and
a sensor cover configured to be attached to the main body, wherein
the sensor cover has a tip with an arcuate shape or an annular shape being greater in size in a radial direction with respect to the sensor, protruding at a tip side of the main body with respect to the sensor, and the sensor cover includes an opening opened at a position corresponding to the sensor on the main body in a longitudinal direction and having a width equal to or greater than a width of the sensor in a side view.

2. The oil deterioration detector comprising:
a sensor configured to measure electrical characteristics of an oil;
a main body having an elongated shape and having the sensor in a sideward-facing orientation at one end of the elongated shape thereof; and
a sensor cover including a base part configured to be attached to the main body, a tip head part having an arcuate shape or an annular shape being greater in size in a radial direction with respect to the sensor, disposed in a manner protruding at a tip side of the main body with respect to the sensor, and a connection part including a first connecting pillar connecting the base part and the tip head part and a second connecting pillar having a width smaller than a width of the first connecting pillar, wherein
the sensor cover is at a first circumferential position where the connection part covers at least a part of the sensor.

3. The oil deterioration detector comprising:
a sensor configured to measure electrical characteristics of an oil;
a main body having an elongated shape and having the sensor in a sideward-facing orientation at one end of the elongated shape thereof; and
a sensor cover including a base part configured to be attached to the main body, a tip head part having an arcuate shape or an annular shape being greater in size in a radial direction with respect to the sensor, disposed in a manner protruding at a tip side of the main body with respect to the sensor, and a connection part connecting the base part and the tip head part at only one place, wherein
the sensor cover is at a first circumferential position where the connection part covers at least a part of the sensor.

4. The oil deterioration detector according to claim 2, wherein the sensor cover is rotatable relative to the main body between the first circumferential position and a second circumferential position where the connection part does not completely cover the sensor.

5. The oil deterioration detector according to claim 4, wherein the sensor cover is rotatable and detachable with respect to the main body by screwing screws.

6. A sensor cover of oil deterioration detector configured to be attached to an oil deterioration detector, the oil deterioration detector comprising a sensor configured to measure electrical characteristics of an oil; and a main body having an elongated shape and having the sensor in a sideward-facing orientation at one end of the elongated shape thereof, and configured to detect a degree of deterioration of oil from the electrical characteristics, wherein
in a state of being attached to the oil deterioration detector, a tip of the sensor cover protrudes at a tip side of the main body, and the tip of the sensor cover has an arcuate shape or an annular shape being equal to or greater in size in a radial direction with respect to the sensor, and the sensor cover includes an opening opened at a position corresponding to the sensor on the main body in a longitudinal direction and having a width wider than a width of the sensor in a side view.

7. A method of measuring degree of oil deterioration for measuring the deterioration degree of an oil heated or kept warm by an IH heating device by an oil deterioration detector, the method comprising:
using an oil deterioration detector comprising a sensor configured to measure electrical characteristics of an oil and a main body having an elongated shape and having the sensor in a sideward-facing orientation at one end of the elongated shape thereof;
bringing the sensor cover into an attached state with the main body of the oil deterioration detector so as the sensor is arranged inside the sensor cover, where the sensor cover is made of a material that generates an eddy current so as to cancel an alternating magnetic flux while the sensor cover is placed in a space where the alternating magnetic flux is generated; and
measuring the electric characteristics with the sensor while the sensor is immersed in the oil at the attached state of the sensor cover.

8. The method of measuring degree of oil deterioration according to claim 7, wherein
the sensor cover comprises a base part configured to be attached to the main body; a tip head part having an arcuate shape or an annular shape being greater in size in a radial direction with respect to the sensor, disposed in a manner protruding at a tip side of the main body with respect to the sensor in a state of being attached to the main body; and a connection part including a first connecting pillar connecting the base part and the tip head part and a second connecting pillar having a width smaller than a width of the first connecting pillar.

9. The method of measuring degree of oil deterioration according to claim 8, wherein
the sensor is oriented toward the side of the main body, and
the sensor cover is in a state in which the connection part is at a first circumferential position covering at least a part of the sensor with respect to the main body.

10. The method of measuring degree of oil deterioration according to claim 9, wherein
the sensor cover is rotatable relative to the main body between the first circumferential position and a second circumferential position where the connection part does not completely cover the sensor;
wherein cleaning of the sensor is performed while the sensor cover positioned at the second circumferential position.

11. An oil deterioration detector comprising:
a sensor configured to measure an electrical characteristics of an oil;
a main body having an elongated shape and having the sensor in a sideward-facing orientation at one end of the elongated shape thereof;
a sensor cover configured to be attached to the main body and is made of a material that generates an eddy current so as to cancel an alternating magnetic flux while the sensor cover is placed in a space where the alternating magnetic flux is generated; wherein
the sensor is arranged inside the sensor cover.

12. The oil deterioration detector according to claim 11, wherein
the main body has the sensor in a sideward-facing orientation with respect to the main body;
wherein the sensor cover includes a tip protruding at a tip side of the main body and the tip of the sensor cover having an arcuate shape or an annular shape being equal to or greater in size in a radial direction with respect to the sensor, and the sensor cover including an opening opened at a position corresponding to the sensor on the main body in a longitudinal direction and having a width wider than a width of the sensor in a side view.

13. The oil deterioration detector according to claim 11, wherein the main body has the sensor in a sideward-facing orientation with respect to the main body;

wherein the sensor cover includes a base part configured to be attached to the main body, a tip head part having an arcuate shape or an annular shape being greater in size in a radial direction with respect to the sensor, disposed in a manner protruding at a tip side of the main body with respect to the sensor, and a connection part including a first connecting pillar connecting the base part and the tip head part and a second connecting pillar having a width smaller than a width of the first connecting pillar, and the sensor cover is at a first circumferential position with respect to the main body where the connection part covers at least a part of the sensor.

14. The oil deterioration detector according to claim 11, wherein the main body has the sensor in a sideward-facing orientation with respect to the main body;

wherein the sensor cover includes a base part configured to be attached to the main body, a tip head part having an arcuate shape or an annular shape being greater in size in a radial direction with respect to the sensor, disposed in a manner protruding at a tip side of the main body with respect to the sensor, and a connection part connecting the base part and the tip head part at only one place, and the sensor cover is at a first circumferential position with respect to the main body where the connection part covers at least a part of the sensor.

15. The oil deterioration detector according to claim 13, wherein the sensor cover is rotatable relative to the main body between the first circumferential position and a second circumferential position where the connection part does not completely cover the sensor.

16. The oil deterioration detector according to claim 11, wherein the sensor cover is rotatable and detachable with respect to the main body by screwing screws.

17. The oil deterioration detector according to claim 3, wherein the sensor cover is rotatable relative to the main body between the first circumferential position and a second circumferential position where the connection part does not completely cover the sensor.

18. The oil deterioration detector according to claim 17, wherein the sensor cover is rotatable and detachable with respect to the main body by screwing screws.

19. The oil deterioration detector according to claim 14, wherein the sensor cover is rotatable relative to the main body between the first circumferential position and a second circumferential position where the connection part does not completely cover the sensor.

\* \* \* \* \*